(12) United States Patent
Miller et al.

(10) Patent No.: US 7,736,346 B2
(45) Date of Patent: Jun. 15, 2010

(54) BIO-INTERVENTIONAL THERAPEUTIC TREATMENTS FOR CARDIOVASCULAR DISEASES

(75) Inventors: Aaron Miller, San Francisco, CA (US); Loren Bentley, Oakland, CA (US); Daniel C. Rosenman, San Francisco, CA (US); Peter A. Altman, San Francisco, CA (US)

(73) Assignee: Biocardia, Inc., San Carlos, CA (US)

( * ) Notice: Subject to any disclaimer, the term of this patent is extended or adjusted under 35 U.S.C. 154(b) by 1010 days.

(21) Appl. No.: 11/253,177

(22) Filed: Oct. 18, 2005

(65) Prior Publication Data
US 2007/0088244 A1    Apr. 19, 2007

(51) Int. Cl.
*A61M 5/00*    (2006.01)

(52) U.S. Cl. .................................................... 604/264

(58) Field of Classification Search ................. 604/22, 604/93.01, 264, 506–507, 509–511, 95.02
See application file for complete search history.

(56) References Cited

U.S. PATENT DOCUMENTS

| | | | |
|---|---|---|---|
| 5,403,311 A * | 4/1995 | Abele et al. .................... | 606/49 |
| 5,527,344 A | 6/1996 | Arzbaecher et al. | |
| 5,928,145 A | 7/1999 | Ocali et al. | |
| 6,102,887 A * | 8/2000 | Altman ........................ | 604/22 |
| 6,193,763 B1 | 2/2001 | Mackin | |
| 6,408,203 B2 | 6/2002 | Mackin | |
| 6,478,776 B1 | 11/2002 | Rosenman et al. | |
| 6,620,139 B1 * | 9/2003 | Plicchi et al. ................ | 604/264 |
| 6,716,196 B2 | 4/2004 | Lesh et al. | |
| 6,878,371 B2 | 4/2005 | Ueno et al. | |
| 7,357,794 B2 | 4/2008 | Makower et al. | |
| 2003/0158519 A1 * | 8/2003 | Epstein et al. ............... | 604/116 |
| 2004/0024371 A1 | 2/2004 | Plicchi et al. | |
| 2004/0161421 A1 | 8/2004 | Komowski et al. | |
| 2004/0199115 A1 | 10/2004 | Rosenman | |
| 2004/0220470 A1 | 11/2004 | Karmarkar et al. | |
| 2006/0135961 A1 | 6/2006 | Rosenman et al. | |

\* cited by examiner

*Primary Examiner*—Nicholas D Lucchesi
*Assistant Examiner*—Christopher D Koharski
(74) *Attorney, Agent, or Firm*—Haugen Law Firm PLLP; Frederick W. Niebuhr

(57) ABSTRACT

Catheter-based systems are disclosed for geometrically and temporally controlled deliveries of fluid agents to the heart. Each system includes an elongate catheter shaft, a tissue penetration element at the shaft distal end, and a handle at the shaft proximal end for manipulating the penetrating element. The penetrating element and a proximate conductive coil provide bipolar sensing electrodes. One version of the system includes a fluid lumen through the penetrating element and a contrast fluid lumen open at the catheter shaft distal end. In other versions, the penetrating element contains two fluid lumens. These systems facilitate tissue mapping and therapeutic agent delivery protocols in which several agents can be simultaneously delivered at a depth within heart tissue, prevented from intermingling until they reach the tissue. Treatment and contrast agents can be delivered simultaneously or temporally spaced, directed to the same region or to different regions separated by intervening tissue.

32 Claims, 8 Drawing Sheets

BIO-INTERVENTIONAL THERAPEUTIC TREATMENTS FOR CARDIOVASCULAR DISEASES

BACKGROUND OF THE INVENTION

The present invention relates to local biotherapeutic delivery in cardiac regions, and more particularly to devices and processes for locally delivering therapeutic agents such as controlled release proteins, cell based therapies, and gene based therapies for treating heart failure, stenosis, ischemia, arrhythmias, hypertrophic cardiomyopathies, infarction, and vulnerable plaque. The invention also relates to therapeutic strategies incorporating percutaneous intramyocardial delivery catheter systems for transendocardial delivery from within the ventricles of the heart, selected biopharmaceutical agents, sustained delivery means, and geometrical and temporal delivery protocols, targeted towards indications within cardiovascular disease, including coronary artery disease (including stenosis, restenosis, vulnerable plaque, and ischemia), congestive heart failure, myocardial infarction, atrial cardiac conduction disorders, and ventricular cardiac conduction disorders.

Coronary Artery Disease (CAD)

Blood flow to the heart muscle can be severely reduced by atherosclerotic disease of the coronary arteries, which accounts for most ischemic heart disease. Insufficient oxygen to the heart muscle as a result of restricted blood flow can lead to myocardial ischemia, and possibly to a heart attack or death. Restoring blood flow is the most effective method to relieve painful ischemic symptoms and to reduce the long-term risk of a heart attack.

Current treatments for coronary artery disease include drug therapy, coronary artery bypass surgery and catheter-based treatments, including angioplasty, atherectomy and coronary stenting.

Restenosis

Today, local drug therapies are delivered from the surfaces of stents to reduce the potential for restenosis after percutaneous transluminal angioplasty, with or without stent placement.

Vulnerable Plaque

In recent years the cause of a myocardial infarction has been identified as thin walled plaques in relatively open vessels. Vulnerable plaques are predisposed to suddenly come free from the artery wall, and may occlude a vessel. Vulnerable plaques often are characterized as having a lipid core and being "hot" in that they are slightly warmer than surrounding tissue. The ability to identify and treat vulnerable plaques before they cause myocardial infarction is in active development.

Cardiac Ischemia

Cardiac ischemia occurs when a coronary artery is partially or completely obstructed, such as due to atherosclerosis. A sudden, severe blockage of a coronary artery may kill part of the heart muscle (heart attack). Cardiac ischemia may also cause an abnormal heart rhythm (arrhythmia), which can lead to fainting or even sudden death. Treatment is directed at improving blood flow to the heart muscle, and may include medication, exercise, angioplasty, and bypass surgery.

Heart Attack/Myocardial Infarction (MI)

A heart attack occurs when a blockage in a coronary artery severely restricts or stops blood flow to a portion of the heart. When blood supply is greatly reduced or stopped for a sufficient time, heart muscle cells die. Heart muscle cells generally lack the ability to multiply to replace the dead cells. After a heart attack, white blood cells migrate into the area and remove the dead heart muscle cells, and fibroblast cells proliferate and form a fibrous collagen scar in the affected region of the heart. Following a heart attack, the heart's ability to maintain normal function will depend on the location of the damage and the amount of damaged tissue.

Current therapeutic treatments for heart attack include drug therapy to dissolve a blood clot immediately following a heart attack, medicines to alleviate symptoms, and certain lifestyle changes, such as an altered diet, increased exercise levels and cessation of smoking.

Congestive Heart Failure (CHF)

Congestive heart failure is caused when the heart is unable to contract adequately to pump blood throughout the body. The normal physiological stimulation of heart function is generated when chemical transmitters known as catecholamines bind with certain receptors on the surfaces of heart cells, triggering a series of events that result in increased heart rate and increased force of contraction. Typically, in congestive heart failure, the heart is unable to respond adequately to catecholamines.

Current treatments for congestive heart failure include drug therapy, and rarely, heart transplantation. Drug treatments generally treat symptoms only, and have a limited effect on the progression of the disease.

Cardiac Conduction System Disorders

The rhythmic contraction of the heart essential for its function as a pump is enabled by the conduction of electrical signals between cells and along specialized conducting networks within the heart such as the sinoatrial node, the atrioventricular node, and the perkinje fibers. To date, disruptions in these conduction pathways have been treated either by tissue ablation to remove a pathway, or by the implantation of devices designed to pace the heart (pacemakers) or to jump start the heart after disorganization of the electrical signals (defibrillators).

One conduction system disorder, atrial fibrillation (AF), may be treated with an atrial defibrillator to deliver energy to the atrium to terminate arrhythmias. However, this therapy is painful, has the potential to initiate life threatening ventricular arrhythmias, and requires an expensive cosmetically undesirable permanent implant.

Doctors have treated atrial fibrillation with drugs administered intravenously or orally. U.S. Pat. No. 5,527,344 (Arzbaecher) describes a pharmacological atrial defibrillator and method for automatically delivering a defibrillating drug into the blood stream upon detection of atrial arrhythmias. The defibrillating drug is injected in a large initial dose followed by a continuous smaller dose. If the injected drug is to have an effective concentration within the heart, a large amount must be injected into the blood stream, risking undesirable side effects in other organs.

Atrial fibrillation also is treated by atrial ablation by heating tissue with RF energy, laser energy, ultrasound energy, by cooling tissue, by surgically cutting the tissue, or by infusing tissue with an ablative medium such as ethanol or phenol.

Arrhythmias similar to atrial fibrillation also are treated with ablation. For example, conduction over the fast and slow pathways of the AV node can occur simultaneously, leading to a double ventricular response from each atrial beat that may present as symptomatic, incessant, and irregular narrow-complex tachycardia which may be misdiagnosed as atrial fibrillation. Slow AV nodal pathway focal ablation can stop tachycardias and restore ventricular function when cardiomyopathy is present. Other arrhythmias may be treated with similar ablative approaches.

There are two general approaches for providing ablative therapy to the heart to treat atrial fibrillation: the long linear ablative lesion approach, and the focal ablation approach. In the long linear ablative lesion approach, heart tissue is killed along a linear pathway, to segment the heart into regions too small to sustain atrial fibrillation. In the focal ablation approach, the heart tissue is killed at a single site, to ablate the region of the heart that prematurely depolarizes and acts as a trigger to initiate atrial fibrillation. Focal ablations remove triggers that initiate atrial fibrillation, often within the pulmonary veins or in the region near the junction of the veins with the left atrial tissue.

Many of these treatments require sensing electrical activity in cardiac tissue to determine whether a particular location is appropriate for a selected treatment, or to measure electrical activity after ablation therapy to determine whether the intended result has been achieved. Frequently there is a need to image tissue surrounding a selected treatment site.

In conjunction with supplying treatment agents locally to a designated site, there is a need for the option to supply several different agents to a given site while ensuring that the agents do not mingle until reaching, or nearly reaching, the treatment site. Finally, in conjunction with using a contrast fluid to fluoroscopically image a treatment site, there is a need for applying an agent to the treatment site in relative isolation from the contrast fluid.

SUMMARY OF THE INVENTION

To address the foregoing needs, there is provided a process for treating a heart for heart failure, including the steps of:

a. using an elongate catheter having a fluid delivery structure at its distal end to guide the fluid delivery structure to a treatment site in a chamber of the heart, and to cause a penetrating element of the fluid delivery component to penetrate surrounding tissue at the treatment site; and b. with the penetrating element so penetrated, supplying a fluid agent including BNP to a location at a depth within the surrounding tissue near the penetrating element via a fluid passage through the fluid supply structure, to provide at the location a matrix for effecting a controlled release of the BNP.

Another aspect of the invention is a process for treating a heart for heart failure, including the steps of:

a. using an elongate catheter having a fluid delivery structure at its distal end to guide the fluid delivery structure to a treatment site in a chamber of the heart, and to cause a penetrating element of the fluid delivery component to penetrate surrounding tissue at the treatment site; and b. with the penetrating element so penetrated, supplying a fluid agent including apelin to a location at a depth within the surrounding tissue near the penetrating element via a fluid passage through the fluid supply structure, to provide at the location a matrix for effecting a controlled release of the apelin.

According to a further aspect of the invention, there is provided a body insertable device for electrically characterizing and treating tissue. The device includes an elongate, flexible catheter body having a proximal end, a distal end, and a lumen extending between the proximal and distal ends. The device further includes an electrically conductive first electrode including a distally located tissue penetrating element adapted to penetrate tissue to a depth within surrounding tissue. A fluid passage through the first electrode is open to an exterior thereof at the tissue penetrating element. The first electrode is coupled to the distal end of the catheter body with the fluid passage fluid-coupled to the lumen. A second electrode comprises an electrically conductive coil disposed along a distal end region of the catheter body in spaced apart and electrically isolated relation to the first electrode. A first elongate electrical conductor, coextensive with the catheter body, electrically couples the first electrode and a first terminal near the proximal end of the catheter body. A second elongate electrical conductor, coextensive with the catheter body, electrically couples the second electrode and a second terminal near the proximal end, whereby electrical differences between the first and second terminals are measurable with the penetrating element so penetrated, to indicate electrical activity in the surrounding tissue.

Another aspect of the present invention is a body insertable apparatus for supplying fluid agents to a depth within tissue. The apparatus includes an elongate, flexible catheter body having a proximal end region, a distal end region, a first lumen running between the proximal and distal end regions, and a second lumen substantially coextensive with and fluid isolated from the first lumen. The apparatus also includes a fluid delivery structure comprising a tissue penetrating element adapted to penetrate tissue to a depth within surrounding tissue. A first fluid passage extends through the fluid delivery structure and is open to and exterior thereof at the tissue penetrating element. A second fluid passage extends therethrough, is fluid isolated from the first fluid passage and also is open to the exterior at the penetrating element. The fluid delivery structure is mounted to the distal end region of the catheter body with the first fluid passage fluid-coupled to the first lumen, and with the second fluid passage fluid-coupled to the second lumen. The fluid delivery structure, with the penetrating element so penetrated, is adapted for a simultaneous delivery of first and second fluid agents to the surrounding tissue from the first and second lumens, respectively.

A further aspect of the invention is a body insertable apparatus for supplying fluid agents to a depth within tissue. The apparatus includes an elongate, flexible catheter body having a proximal end region, a distal end region, a first lumen running between the proximal and distal end regions, and a second lumen substantially coextensive with and fluid isolated from the first lumen. The apparatus further includes a fluid delivery structure comprising a base, and a tissue penetrating element extending distally from the base and adapted to penetrate tissue to a depth within surrounding tissue. A first fluid passage extends through the fluid delivery structure and is open to and exterior thereof at the tissue penetrating element. A second fluid passage extends therethrough and is open to the exterior at the base. The fluid delivery structure is mounted to the distal end region of the catheter body with the first fluid passage fluid-coupled to the first lumen and with the second fluid passage fluid-coupled to the second lumen. The fluid delivery structure, with the penetrating element so penetrated, is adapted for delivery of a first fluid agent to a first depth within the surrounding tissue and delivery of a second fluid agent to a region of the surrounding tissue having a second depth less than the first depth.

A further aspect of the invention is a process for locally treating tissue at a treatment site and visualizing the treatment site, including:

a. using an elongate catheter having a fluid delivery component at its distal end to guide the fluid delivery component to a treatment site, and to cause a penetrating element of the fluid delivery component to penetrate surrounding tissue at the treatment site;

b. with the penetrating element so penetrated, supplying a contrast fluid to a first location in the tissue proximate the base via a first fluid passage through the fluid supply component; and c. further with the penetrating element so penetrated, supplying a fluid agent to a second location in the tissue at a depth within the tissue proximate the penetrating element via a second fluid passage through the fluid supply component.

Another aspect of the invention is a process for simultaneously delivering a plurality of fluid agents at a depth within tissue at a selected treatment site inside the body, including:

a. guiding a fluid supply structure to an intended treatment site inside the body, and causing a tissue penetrating element of the structure to penetrate tissue at the treatment site;

b. with the penetrating element so penetrated, supplying a first fluid agent to the tissue via a first fluid passage through the fluid supply structure open to an exterior of the fluid supply structure at the penetrating element, thus to supply the first fluid agent at a depth within the tissue; and c. simultaneously, supplying a second fluid agent via a second fluid passage through the fluid supply structure coaxial with the first fluid passage and open to the exterior of the fluid supply structure at the penetrating element, thus to prevent any substantial intermingling of the first and second fluid agents until they reach the surrounding tissue.

IN THE DRAWINGS

Further features and advantages will become apparent upon consideration of the following detailed description and drawings, in which.

DETAILED DESCRIPTION OF THE PREFERRED EMBODIMENTS

Figure 1:
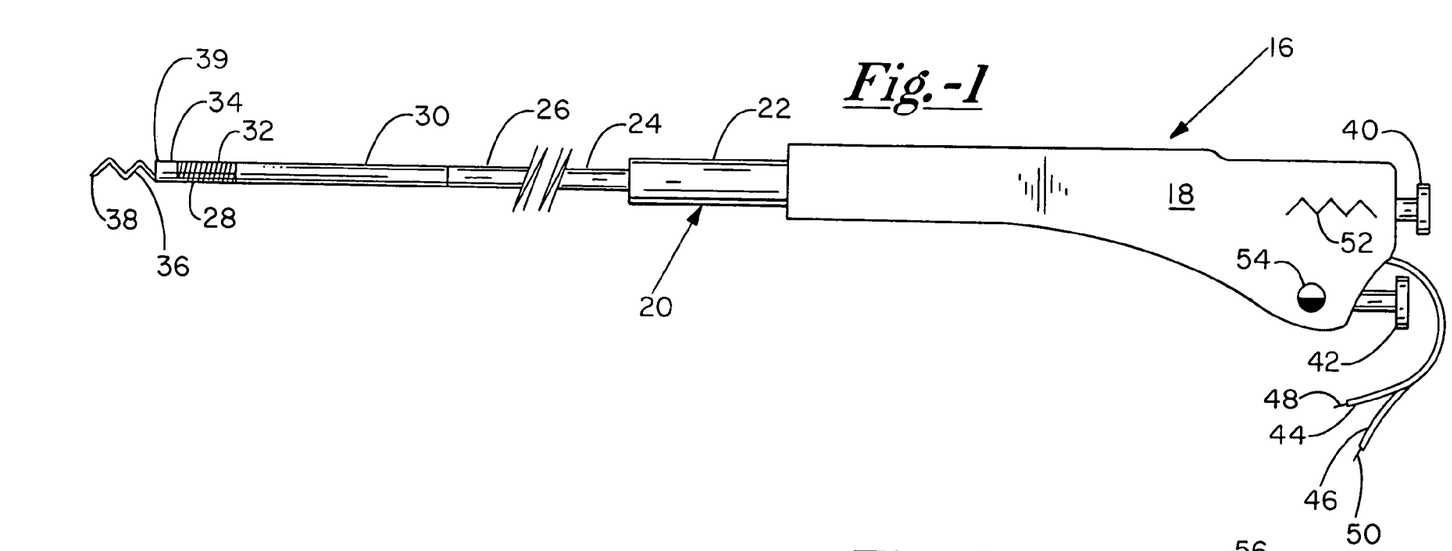
FIG. 1 is a side elevation of a catheter-based fluid agent infusion system constructed according to the present invention.

Turning now to the drawings, FIG. 1 shows a catheter-based system 16 for delivering liquid therapeutic agents to body tissue. While system 16 is described primarily in connection with treating heart tissue, the system can be configured to treat tissues in the brain, liver, kidney, lung, intestine, spleen, and bladder.

The system includes a proximal handle 18, and a catheter shaft 20 extending distally from the handle. The catheter shaft includes a proximal region 22 formed of PEEK, PEBAK or another suitable polymer and having a diameter larger than that of the rest of shaft 20. The proximal region provides strain relief for the junction with handle 18, and docks with the hand piece of a guide catheter (not shown) used to direct shaft 20 to an intended treatment site in the heart. The shaft further includes an elongate medial region 24 formed of polyimide with an embedded braid formed of metal, e.g. stainless steel, MP35N, titanium, or Nitinol (brand name) titanium-nickel alloy. Optionally and as shown, the shaft further includes a distal region 26 preferably formed of Pebax (brand name) polyether block amide, to provide a lower durometer section for enhanced flexibility.

An electrically conductive coil 28, preferably an eight-filer coil of 0.006 inch diameter wires of No. 304 stainless steel, is coupled to and extends distally from distal region 26. Over a portion of its length, coil 28 may be surrounded by an electrically insulative jacket 30, preferably a heat shrink polyester. An exposed region of coil 28, distally of jacket 30, provides an electrode 32. Alternatively, the entire coil may be exposed.

A distal end of coil 28 is encapsulated by a body of epoxy forming a base 34, which also encapsulates a proximal portion of a tissue penetrating element in the form of a helix 36. A fluid passage (not shown) runs through the helix from the embedded proximal portion to a distal tip 38 where the passage is open to the exterior of the helix. Helix 36 and base 34 together provide a fluid supply structure 39 for delivering fluids to tissue into which helix 36 is penetrated. At the proximal end of handle 18 are a pair of proximal fluid ports 40 and 42, and a pair of electrical leads 44 and 46 in the form of copper wires coated with polyimide and having respective proximal end terminals 48 and 50. Proximal port 40 is fluid coupled to the fluid passage that runs through helix 36, e.g. by a tube (not shown) contained within handle 18 and shaft 20. A helix symbol 52 is applied to the handle near port 40, to indicate the fluid coupling. Proximal port 42 is fluid coupled to a fluid passage that runs through base 34. A symbol 54, applied to the handle near port 42, indicates the fluid path intended for contrast fluid.

Lead 44, contained within handle 18 and shaft 20, runs the length of the catheter shaft for an electrical coupling to helix 36. Similarly, lead 46 runs distally through the handle and catheter shaft for an electrical coupling to coil 28. Helix 36 thus cooperates with coil electrode 32 to provide an electrode pair for bipolar sending electrical activity in tissue. Differences in electrical potential between terminals 48 and 50, with helix 36 embedded into or otherwise in contact with tissue at a given treatment site, provide bipolar measurements of electrical activity in tissue at the site.

Figures 3A, 3B, 3C:
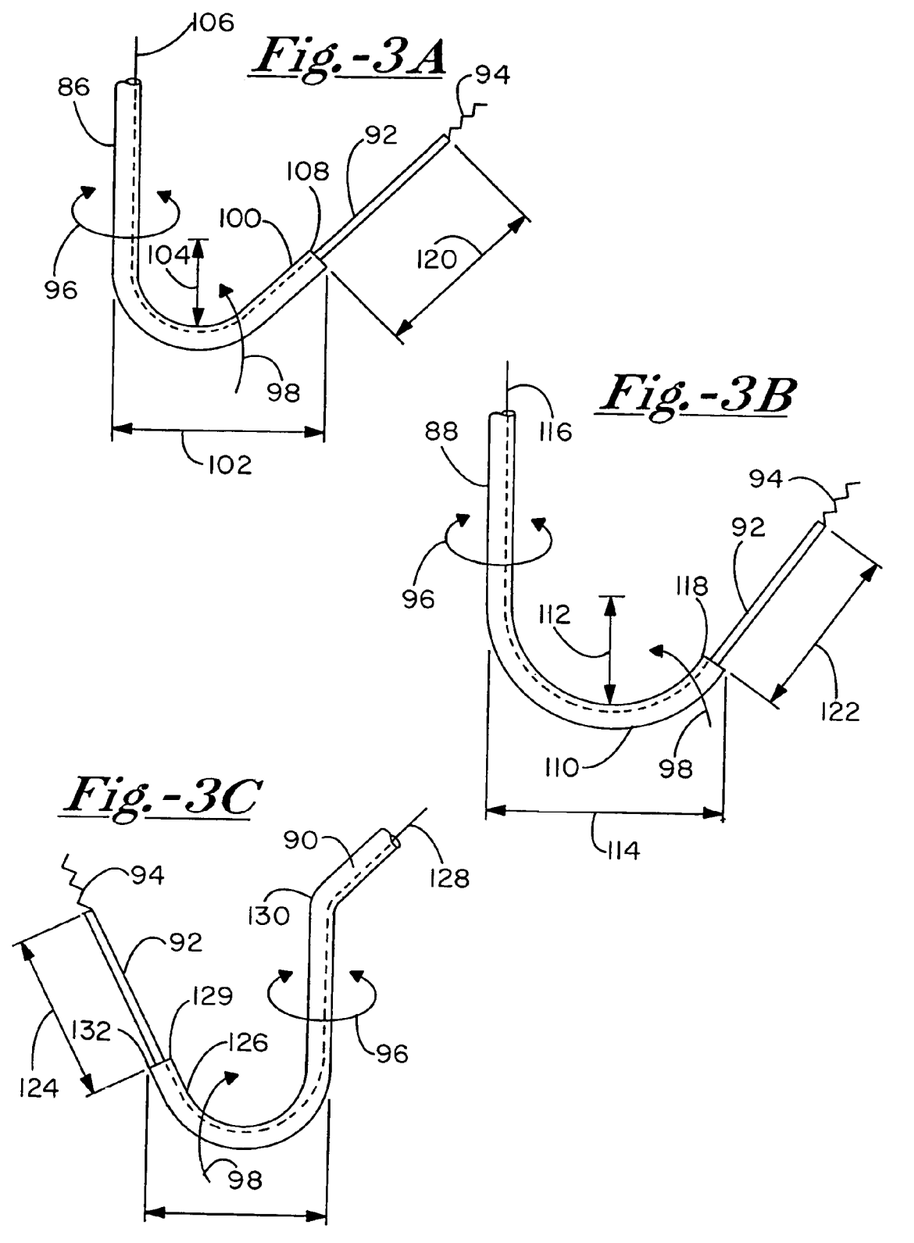
FIGS. 3A, 3B and 3C show distal regions of three alternative embodiment guide catheters containing an infusion catheter shaft.

System 16 can be used in a variety of processes for treating heart tissue with fluid agents. Initially a guidewire is advanced translumenally until its distal end is near the intended treatment site. Next, a guide catheter such as the Morph (brand name) deflectable catheter manufactured by Biocardia, Inc. is advanced over the guidewire to the ventricle, for example introduced into a patient's femoral artery, advanced through the aortic arch, then through the aortic valve and into the left ventricular chamber, and oriented toward the target tissue. After withdrawal of the guidewire, catheter shaft 20 is advanced distally through a lumen in the guide catheter, until a distal end region including helix 36 and at least a distal portion of coil 28 emerge from the distal tip of the guide catheter, as illustrated in FIGS. 3A-3C. As can be understood in conjunction with these figures, handle 18 and the guide catheter can be manipulated outside the body to control the guide catheter orientation, the amount of distal region deflection, and the reach or distal extension of catheter shaft 20 beyond the guide catheter distal tip, to selectively position fluid supply structure 39 and penetrate helix 36 into surrounding tissue for sensing electrical activity, infusing a fluid treatment agent, or both.

For sensing electrical activity over a broader region of tissue or for a more general application of the fluid agent, catheter shaft 20 and the guide catheter are manipulated to systematically reposition the fluid delivery structure at several or multiple sites.

Upon engagement, a contrast medium can be infused through the contrast port for visualizing the location of the fluid supply structure with respect to the tissue. The contrast medium also provides a means to mark the tissue locally for visualizing the delivery site. The contrast medium delivery site is near the tissue surface, separated by tissue from the site of biotherapeutic delivery at a depth within the tissue. As a result, interactions between the contrast medium and the treatment agent are minimized or avoided.

Figure 2:
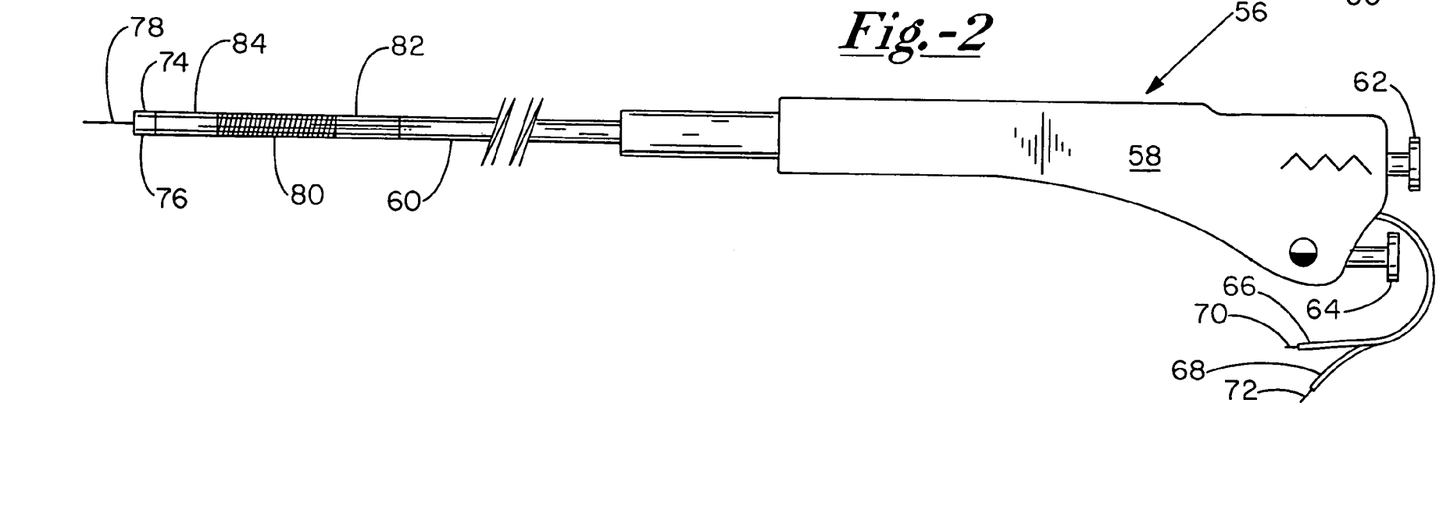
FIG. 2 is a side elevation of an alternative embodiment catheter-based infusion system.

FIG. 2 shows an alternative embodiment catheter-based infusion system 56 including a handle 58, a catheter shaft 60, proximal fluid ports 62 and 64, leads 66 and 68, and terminals 70 and 72 similar to their counterparts in system 16. A fluid supply structure 74 of system 56 includes a base 76 at the catheter shaft distal end, and a linear (or alternatively slightly curved) needle 78 extending distally from the base. An electrically conductive coil 80, surrounded at its proximal and distal ends by insulative jackets 82 and 84 respectively, has a longer exposed length, thus a larger exposed surface area, than coil 28 in system 16. In preferred versions of systems 16 and 56, the insulative spacing between electrodes 36 and 78 at the shaft distal end, and their associated coils 28 and 80, is 10 mm. The intra-electrode spacing, and the proximal electrode length (exposed coil surface area) can be selected in accordance with the procedure at hand.

As compared to system 16, use of system 56 is advantageous in situations where the tissue is relatively stable, where multiple repeated infusions are required, or where the operator lacks experience with helical tissue engagement.

Cardiac signals have advantages as described in U.S. Pat. No. 6,716,196 (Lesh) for mapping target sites for delivery. Target sites may include cardiac conduction system locations such as the sinoatrial node, the atrioventricular node, the bundle of HIS, the crista terminalis, the pulmonary veins, fast and slow pathways of conduction, and other regions where the electrical signals provide information useful in guiding therapy.

Further, because the distal electrode (preferably a helix) is fixed to the tissue, it is also possible to pace the heart tissue at ever decreasing voltages to determine either the viability of the tissue, or the effect of fluid agents on contraction viability. Tissue that is less viable or more distant from the electrode will require higher voltages to capture and pace the heart. The use of higher voltages through these systems tends to enhance the uptake of potential biotherapeutic agents into cellular tissue through a process called electroporation. As the heart may be paced at higher voltages during biotherapeutic delivery, these systems can prevent potentially life threatening arrhythmias that might otherwise occur because of poor timing of the electrical stimulation. Whether the electrodes are used for pacing or sensing, they can be used to control the timing of fluid agent infusion with respect to the cardiac cycle, e.g. to deliver during diastoles when the heart is relaxing and expanding.

FIG. 3A, 3B, and 3C respectively show distal portions of guide catheters 86, 88 and 90, each with a catheter shaft 92 and fluid supply structure 94 advanced beyond the distal tip of the guide catheter. Catheters 86-90 can be similar to the Morph (brand name) guide catheter manufactured by BioCardia, Inc. Unlike, other transendocardial systems, the preferred operation of these catheter systems is not to advance the guide against the ventricular wall where it can become trapped within the trabeculae. Instead, the deflectable guide catheter rotates freely within the ventricle and points toward the target region of interest. Through rotation as at 96, and deflection as at 98, different regions within the ventricle are accessible. The geometry of the optimal deflectable guide catheter is selected with respect to the tissue region for optimal navigation. For example, in patients without severe dilation of the ventricular chamber due to cardiovascular disease, deflectable guide catheter 86 with a shorter deflectable segment 100 enables the catheter to be manipulated within the ventricle. The short deflectable segment entails a shorter sweep length 102 and a smaller radius of curvature 104. A pull wire 106, contained within guide catheter 86 and extending proximally beyond a proximal end (not shown) of the guide catheter, is attached to the distal end of the guide catheter at point 108. The operator pulls wire 106 proximally to generate the tensile force to deflectable segment 100 of the catheter from a linear configuration in which segment 100 is aligned axially with the rest of catheter 86, to a deflected configuration such as that shown in FIG. 3A.

FIG. 3B shows guide catheter 88 with a longer deflectable segment 110 with a larger radius of curvature 112 and sweep length 114. A pull wire 116, attached to guide catheter 88 at a point 118 near its distal end, is pulled proximally to defect segment 110 from a linear configuration to a deflected configuration as shown.

For ventricular chambers with normal dimensions, a catheter with a sweep of 20 to 35 mm is appropriate. In larger, dilated ventricles, 35 mm to 60 mm is desirable. A physician typically employs noninvasive transendocardial echo to determine the size of the heart, and can preselect the appropriate guide catheter to address the particular ventricular geometry.

The length of catheter shaft 92 which extends beyond the deflectable guide catheter is called the reach, and is shown with respect to the catheters at 120, 122 and 124, respectively. Increasing the available reach of the catheter facilitates accessing different regions in larger volume ventricles or in organs such as the stomach and bowel. There is a tradeoff, in that increased reach often requires greater column strength in the distal end of the catheter shaft for acceptable control over engagement and penetration of the tissue. Excessive reach may be sometimes undesirable, particularly when the tissue is in motion such as within the beating left ventricle of the heart. Preferred systems set a distal coil length (which also facilitates bending through the deflectable catheter) such that the maximum available reach is 4 to 6 cm.

Deflectable guide catheter selection for transendocardial delivery may also be based on the target region for delivery. For transendocardial delivery in the left ventricle, the guide catheter is advanced around the aortic arch through the aortic valve and into the left ventricular chamber. As the pull wire requires more force to increase its axial length than an equivalently sized cross section of catheter body, the axis of the pull wire tends to lie on the inside of the curve across the aortic arch. This orientation is shown in FIG. 3A and FIG. 3B where pull wires 106 and 116 cause deflection of deflectable segments 100 and 110, respectively. Previous devices have involved spiraling the pull wire through the curve of the aortic arch. The present invention addresses variations in aortic arch geometries, particularly for targeting the ventricular septum.

For example, the alignment of the distal segment is altered as shown in FIG. 3c where deflectable guide catheter 90 is configured so that the wire will lie on the inside of the aortic arch, and a deflectable segment 126 is oriented to deflect toward a septal target. As compared to the pull wires used with catheters 86 and 88, a pull wire 128 is connected to the opposite side of deflection segment 126 at a point 129. The point differs by 180 degrees from that in FIGS. 3A and 3B. To provide room for segment 126 to deflect in this septal orientation, a bend 130 of about 30 degrees is formed in the catheter approximately 6 cm to 9 cm proximally of a distal tip 132 of the catheter, i.e. near where the catheter passes through the aortic valve. In the same way, other deflectable guide catheter systems can be designed to target other quadrants of the ventricle. For example, in addition to guide catheter 90 configured for a deflection toward the septum and either of catheters 86 and 88 configured for a deflection away from the septum, third and fourth guide catheters can be configured for "intermediate" deflection angularly spaced 90 degrees from the preceding directions and opposite each other. Each catheter is predesigned to target a given quadrant. The rotation, deflection, and reach are used to manipulate the penetrating electrode within the target quadrant of the heart. Operators will have different preferences, and different delivery strategies may suggest preferences for different guide systems for navigating within the heart.

Figure 4:
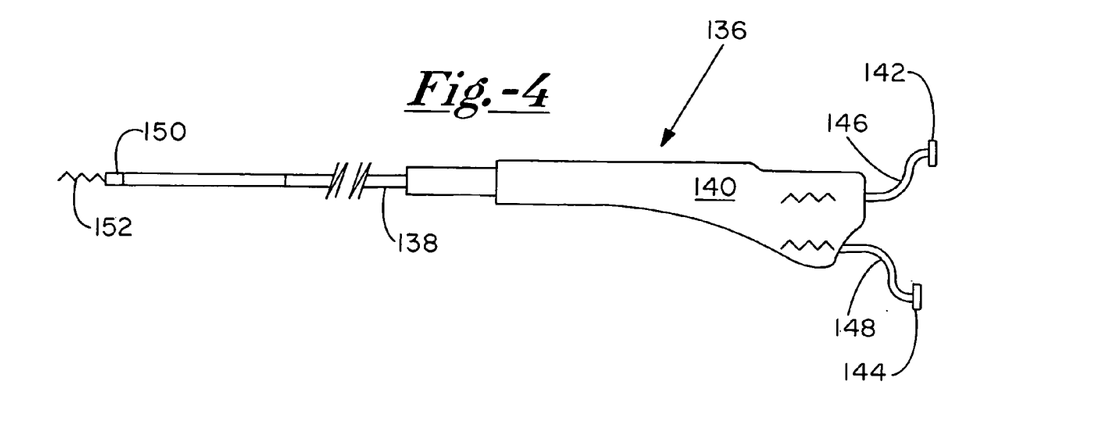
FIG. 4 is a side elevation of another alternative embodiment catheter-based infusion system.

In some procedures it is necessary or advantageous to deliver two fluid agents to the distal tip of the penetrating element and into tissue. FIG. 4 shows a catheter-based tissue infusion system 136 including a catheter shaft 138 and a handle 140 similar to their counterparts in systems 16 and 56. Handle 140 has two proximal fluid ports 142 and 144 including extension tubes 146 and 148 respectively. The proximal extension tubes facilitate connection to a fixture that holds multiple syringes for simultaneous delivery of two or more fluid agents. The fluids provided to ports 142 and 144 travel the length of catheter shaft 138, and are discharged through a fluid supply structure 150 including a tissue penetrating element in the form of a helix 152. The fluids do not mix in the catheter or in the helix, so that mixing occurs within the tissue.

Figure 5:
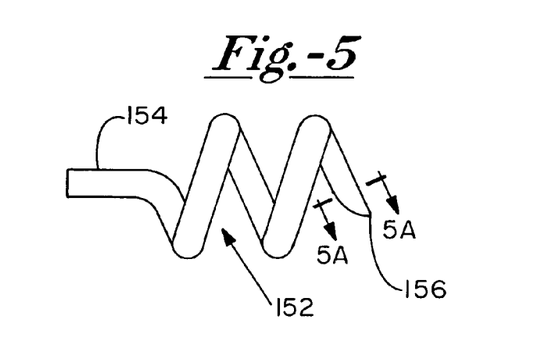
FIG. 5 is a side elevation showing a helical penetration element of the catheter-based infusion system of FIG. 4.

As seen in FIG. 5, helix 152 includes an axially extending proximal shaft 154 and a sharp distal penetrating tip 156. The helix is a bilumen penetrating element in the sense that two separate fluid passages, each coupled to one of proximal fluid ports 142 and 144, run the length of helix 152.

Figures 5A, 5B:
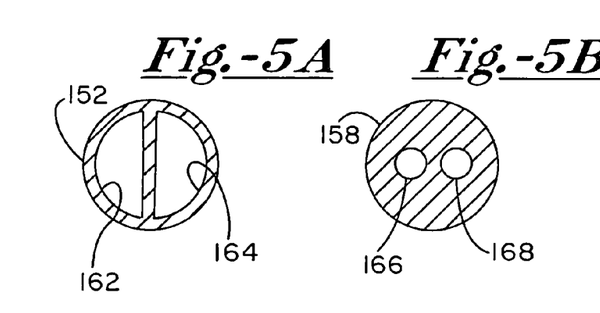
FIGS. 5A-5C are sectional views taken along the line A-A in FIG. 5, illustrating three alternative approaches for providing fluid passages through the penetration element.
Figure 5C:
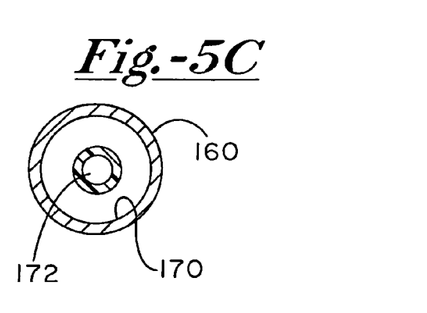

FIG. 5A-5C show helix 152 and two alternative bitumen penetrating elements 158 and 160. Helix 152 has D-shaped lumens 162 and 164 that maximize the "wetted perimeter" of the lumens for minimum fluid resistance, or more precisely, the hydraulic radius determined by the equation $R_h = A/P$ where A is the cross sectional area and P is the perimeter. This result can also be obtained by welding or brazing two flattened tubes together. Penetrating element 158 is a coextruded tube with interior lumens 166 and 168. In this design the mechanical integrity of the structure is favored over maximizing the hydraulic radius. FIG. 5C shows penetrating element 160 with coaxial lumens 170 and 172. This is a preferred embodiment, as the central lumen may be a nonstructural polymeric tube sized for optimum fluid resistance. In each of penetrating elements 152. 158 and 160, the lumens terminate simultaneously at the distal end. In elements 152 and 158, the sharp distal penetrating tip is formed on both lumens simultaneously. In penetrating element 160, the tip may be formed either before or after the central lumen is positioned.

In each of these embodiments, removal of the barrier between the two lumens for a short length near the tip would provide a mixing length within the penetrating element. In the coaxial embodiment this could be accomplished by cutting the polymeric tube short of the helix distal tip. The distance proximal to the tip would correlate to the degree of mixing desired.

Dual lumen discharge at the distal tip of the penetrating element has several advantages. Delivering a small aliquot of a contrast medium through one lumen facilitates confirming the nature of the target tissue by fluoroscopy or MRI, prior to delivering a biotherapeutic agent through the second lumen. This approach may be used to confirm that the fluid supply structure is appropriately positioned. In addition, delivering contrast fluid would indicate whether the tissue bed has rapid venous or lymphatic drainage, and thus is inappropriate for delivery of the biotherapeutic agent. This would essentially provide qualitative pharmacokinetics before each delivery. Further, should one lumen become clogged, the second lumen could be used.

Another advantage is that two components can be delivered in a manner that insures their mixing within the tissue. This can be useful for components that react within the tissues, e.g. fibrin sealants such as Baxter's TISSEEL VH Fibrin Sealant (brand name) or Omrix Biopharmaceuticals Crossseal (brand name). Dual port delivery facilitates the use of two part reagents designed to form a viscoelastic and solid material to increase local structural stability, or provide a controlled release matrix for a desired temporal and spatial delivery of cell, gene, protein, and small molecule therapeutics. Biluminal delivery of two part fluidics whose interaction results in higher viscosity or less fluidity provides for mixing within the tissue, reducing the risk that the catheter will become clogged by the increase in viscosity or decrease in fluidity.

Mixing within tissue raises the possibility of delivering fluid agents that have marked differences in viscosity. Good mixing of multicomponent fluids within tissue presupposes their viscosities to be closely matched, i.e. differing by no more than 25 percent. If agents to be mixed within tissue are not viscosity matched, the less viscous agent will migrate more rapidly away from the delivery site through the available microcirculatory pathways.

System 136 uses, as a contrast media lumen, the second fluidic lumen to the distal tip of the penetrating element. This differs from systems 16 and 56 in that the second fluidic lumen replaces the separate fluid path for delivery of contrast media to the base of the penetrating element. The larger cross sectional area conduits exhibit less resistance in conveying viscous materials and reagents such as gels, controlled release and bioerodable particulate slurries and suspensions, and cell slurries and suspensions.

Figure 6:
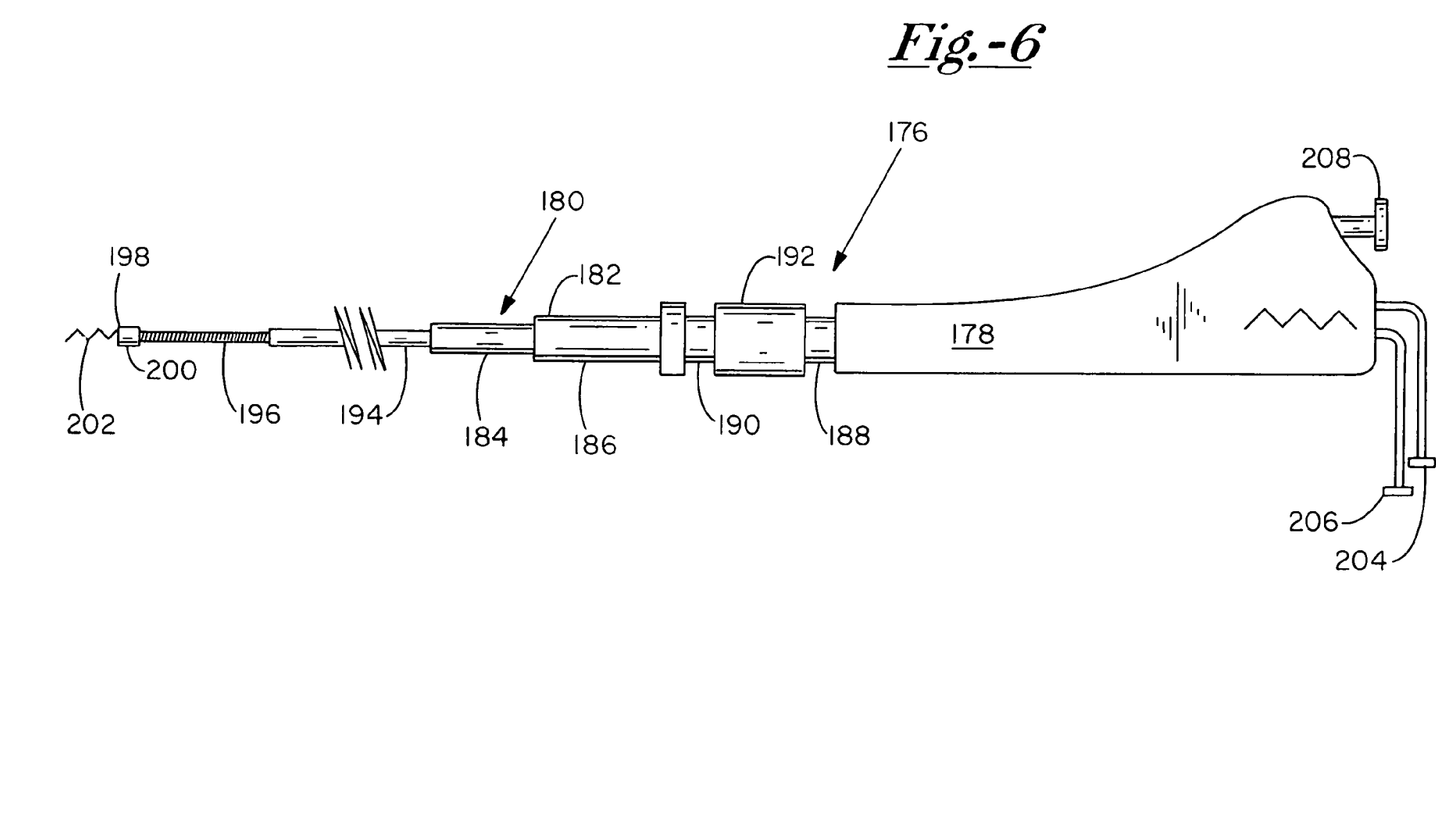
FIG. 6 is a side elevation of a further alternative embodiment catheter-based infusion system.

FIG. 6 shows a trilumen interstitial catheter-based infusion system 176 with bipolar sensing. System 176 includes a proximal handle 178 and a catheter shaft 180 extending distally from the handle. The catheter shaft has a proximal portion 182 including a strain relief member 184 (e.g. formed of PEEK) coupled to the handle, and several components surrounding the strain relief member including an axially slideable extension control section 186 also formed of PEEK, a proximal ring electrode 188, and a distal ring electrode 190. The ring electrodes are separated by an insulative spacer 192 formed of PEEK or another suitable polymer. Axial movement of control section 186 governs the reach, i.e. the distance that catheter shaft 180 extends distally beyond the distal tip of a guide catheter.

A medial shaft region 194 extends distally from strain relief member 184, to a point of joinder with an electrically conductive helical coil 196. A fluid supply structure 198 is mounted at the distal end of the coil, and includes an electrically insulative base 200 and an electrically conductive penetration element in the form of a helix 202 extended distally from the base. Base 200 functions as an electrically insulated spacer between helix 202 and coil 196, and has an axial length of about 1 cm.

Proximal ring electrode 188 is electrically coupled to coil 196, while distal ring electrode 190 is electrically coupled to helix 202. Thus, electrical differences between the ring electrodes indicate electrical activity in tissue contacting and surrounding helix 202. At the proximal end of handle 178 are proximal fluid ports 204 and 206, fluid coupled to separate fluid paths running through helix 202. A proximal fluid port 208 is fluid coupled to a fluid passage through base 200 for providing a contrast medium to tissue near the base.

Ring electrodes 188 and 190 are made of No. 316 L stainless steel or another conductive metal appropriate for catheter electrical connections. Each of the ring electrodes is 0.150 inches in length, with a diameter of 0.110 inches. Spacer 192 has a length of 0.325 inches and a diameter of 0.125 inches. Extension control section 186 is axially moveable over a range of 1.5 inches, but the range can be larger to address certain applications where more reach is required, such as in dilated hearts. Strain relief member 184 is slightly less than 3.5 inches in length.

Figure 7:
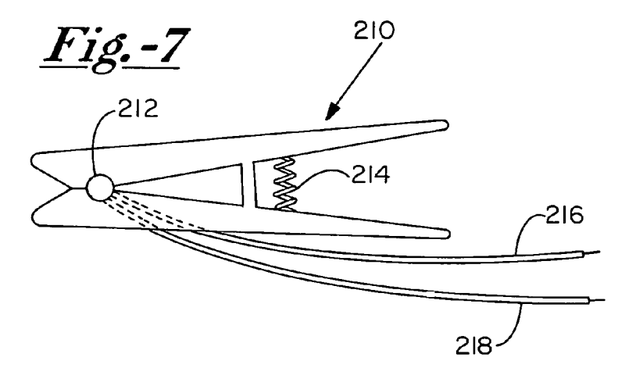
FIG. 7 is a side elevation of an electrode clamp used in the system of FIG. 6.

Electrical connection to ring electrodes 188 and 190 is accomplished with a clothespin type electrode clamp 210 shown in FIG. 7. The clamp has two spaced apart, electrically isolated contacts 212 which close over ring electrodes 188 and 190 while accommodating insulative spacer 192. A compression spring 214 urges the clamp into closure about the ring electrodes. The clamp couples electrodes 188 and 190 respectively to two external leads 216 and 218. When appropriate during a procedure, clamp 210 is placed about catheter shaft 180 to enable measurement of electrical activity in tissue. Clamp 210 is rotatable relative to the catheter shaft while closed, allowing the operator to measure electrical potentials between leads 216 and 218 (and thus between ring the electrodes) while rotating catheter shaft 180 to alternatively penetrate helix 202 into tissue and remove the helix from tissue.

Figure 8:
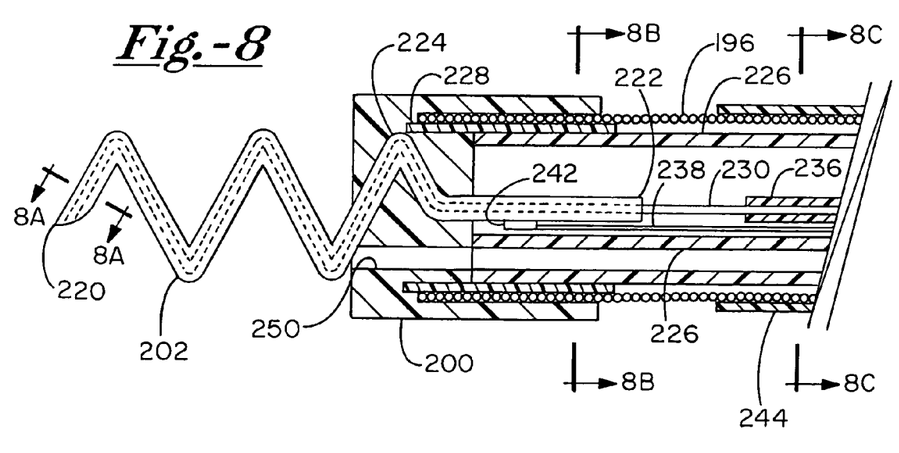
FIG. 8 is an enlarged sectional view showing a distal region of the system shown in FIG. 6.

FIG. 8 is a more detailed view of a distal end region of system 176. Helix 202 is shown to include a sharp distal tip 220 and an axial proximal shaft 222. The proximal shaft, along with part of a proximal turn 224 of the helix, is encapsulated in base 200 which preferably is formed of an electrically insulative potting adhesive such as Loctite (brand name) M-21 HP 811. Several other components at their distal end regions are embedded in base 200, e.g. coil 196, a dual lumen tube 226, and a polyimide jacket 228 surrounding tube 226 and surrounded by coil 196.

Figure 8A:
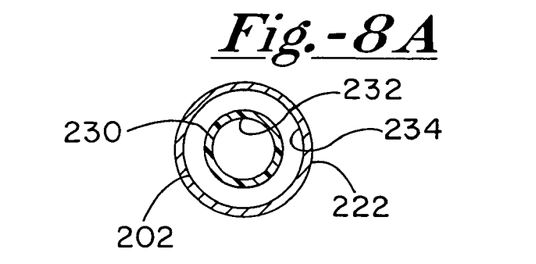
FIGS. 8A-8C are sectional views taken along the lines A-A, B-B and C-C in FIG. 8, respectively.

A fluid passage runs through helix 202 from proximal shaft 222 of the helix to distal tip 220. An inner tube 230 is contained in the fluid passage substantially along the entire passage length, and cooperates with the helix to form two lumens (FIG. 8A) for conducting fluids through the helix: a circular central lumen 232, and an annular lumen 234 surrounding the inner tube. Helix 202 preferably is formed of No. 304 stainless steel and has an outer diameter of 0.0020 inches. Inner tube 230 preferably is formed of polyimide, and its diameter is selected such that lumen 232 has a smaller cross-sectional area than annular lumen 234, although inner tube 230 can be selected to provide lumens 232 and 234 of substantially the same size, if desired.

Inner tube 230 extends proximally from shaft 222 of the helix, toward and into a single lumen tube 236. A UV curable adhesive, e.g. Loctite 3301, is used to bond the proximal end of tube 230 to the distal end of tube 236. Tubes 230 and 236, along with an internal lead 238, are contained in a D-shaped lumen 240 of dual lumen tube 226. Lead 238, preferably a 0.004 inch diameter copper wire coated with polyimide, is mechanically and electrically coupled to proximal shaft 222 of the helix by a solder joint 242.

Coil 196, like coil 28, preferably is an eight filar coil of 0.006 inch diameter wires of No. 304 stainless steel. Dual lumen tube 226 and single lumen tube 236 preferably are formed of a transparent thermoplastic polyamide such as that available from EMS-Grivory under the name Grilamid TR55LX. After lead 238 is attached to shaft 222, dual lumen tube 226 is attached to shaft 222 by a UV curable adhesive, e.g. Loctite 3301. Proximally of base 200, coil 196 may be surrounded by an electrically insulative jacket 244 formed of a heat shrink polyester with a wall thickness of 0.00025 inches. The outside diameter of the catheter shaft along jacket 244 is 0.066 inches.

Figure 8B:
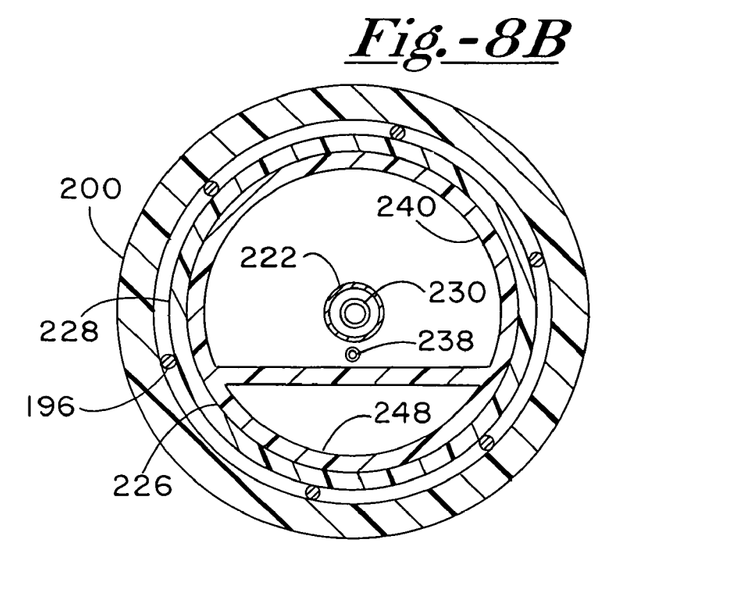

As seen in FIG. 8B, inner tube 230 and proximal shaft 222 of the helix are contained within lumen 240 of the dual lumen tube. Lumen 232 of the inner tube is fluid coupled to a lumen 246 of single lumen tube 236. Annular lumen 234 is fluid coupled to D-shaped lumen 240. Lead 238 also is contained within this D-shaped lumen. The other lumen in tube 226, a D-shaped lumen 248, is fluid coupled to a fluid passage 250 through base 200 to provide part of the fluid path for contrast media. Radially outward of the fluid pathways, dual lumen tube 226 is surrounded by jacket 228, which in turn is surrounded by coil 196 and the outer region of base 200.

Figure 8C:
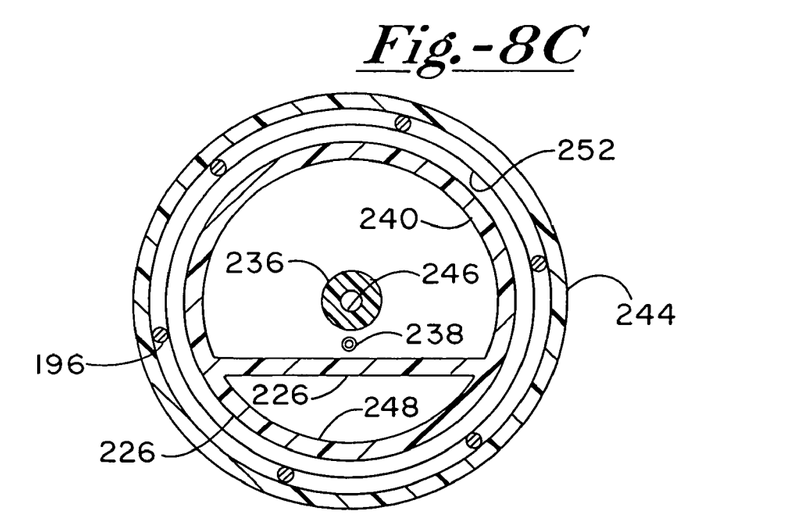

As seen in FIG. 8C, the region of catheter shaft 180 proximal to the connection of tubes 230 and 236 includes single lumen tube 236 and lead 238 disposed within lumen 240, and dual lumen tube 226 disposed within a lumen 252 formed by surrounding coil 196 and polyester heat shrink tube 244.

Figure 9:
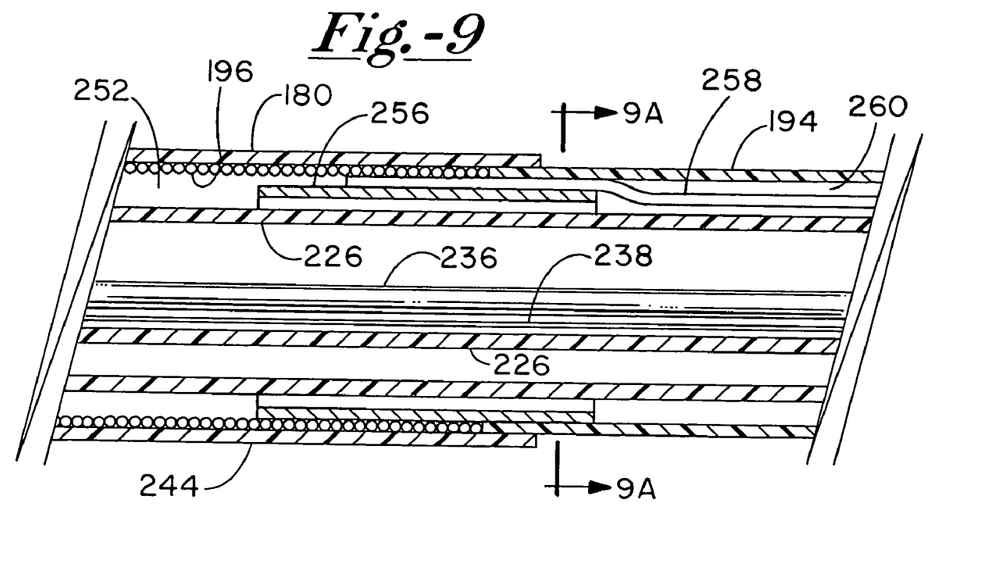
FIG. 9 is a sectional view showing a medial region of the system shown in FIG. 6.

FIG. 9 shows catheter shaft 180 in section along a region including the junction of coil 196 and braided polyimide tubing (medial shaft region) 194. Heat shrink tube 244 may surround the coil and has a wall thickness of 0.00025 inches. Coil 196 and medial region 194 surround a 0.053 inch diameter tubular bushing 256 made of No. 304 stainless steel. The coil and medial region tubing are bonded to the bushing with Loctite 4013 adhesive. An internal lead 258, a 0.004 inch diameter polyimide coated copper wire, is attached to coil 196 and bushing 256 with silver solder. The lead extends proximally from between medial region tubing 194 and the bushing, into a lumen 260 of medial region. Internal lead 238 is soldered or otherwise electrically coupled to distal ring electrode 190. Similarly, internal lead 258 is coupled to proximal ring electrode 188.

Figure 9A:
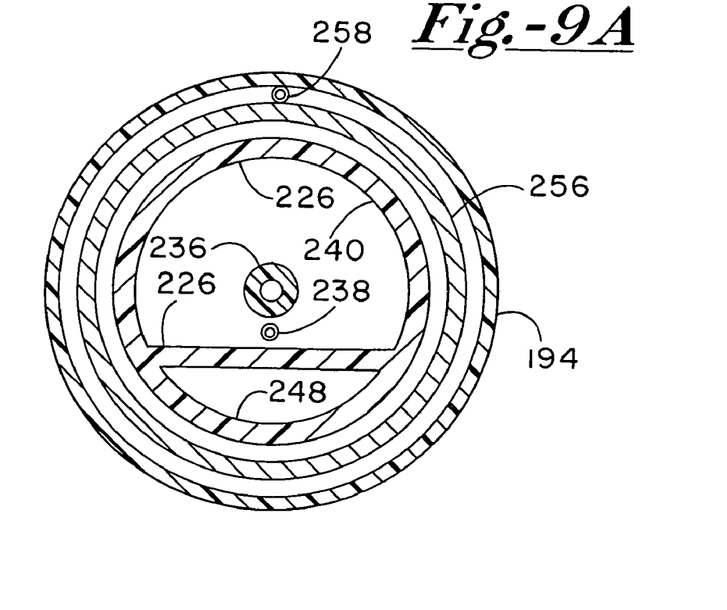
FIG. 9A is a sectional view taken along the line A-A in FIG. 9.

FIG. 9A shows the coil/medial region coupling proximally of heat shrink tube 244 and coil 196. Dual lumen tube 226 passes through bushing 256, with medial region tubing 194 surrounding the bushing. D-shaped lumen 240 contains single lumen tube 236 and lead 238. Outside of the contained components, lumen 240 provides the conduit to annular lumen 234 in helix 202. D-shaped lumen 248 is fluid coupled for conducting contrast media to fluid passage 250 through base 200. Lead 258 is disposed between bushing 256 and tubing 194.

Figure 10:
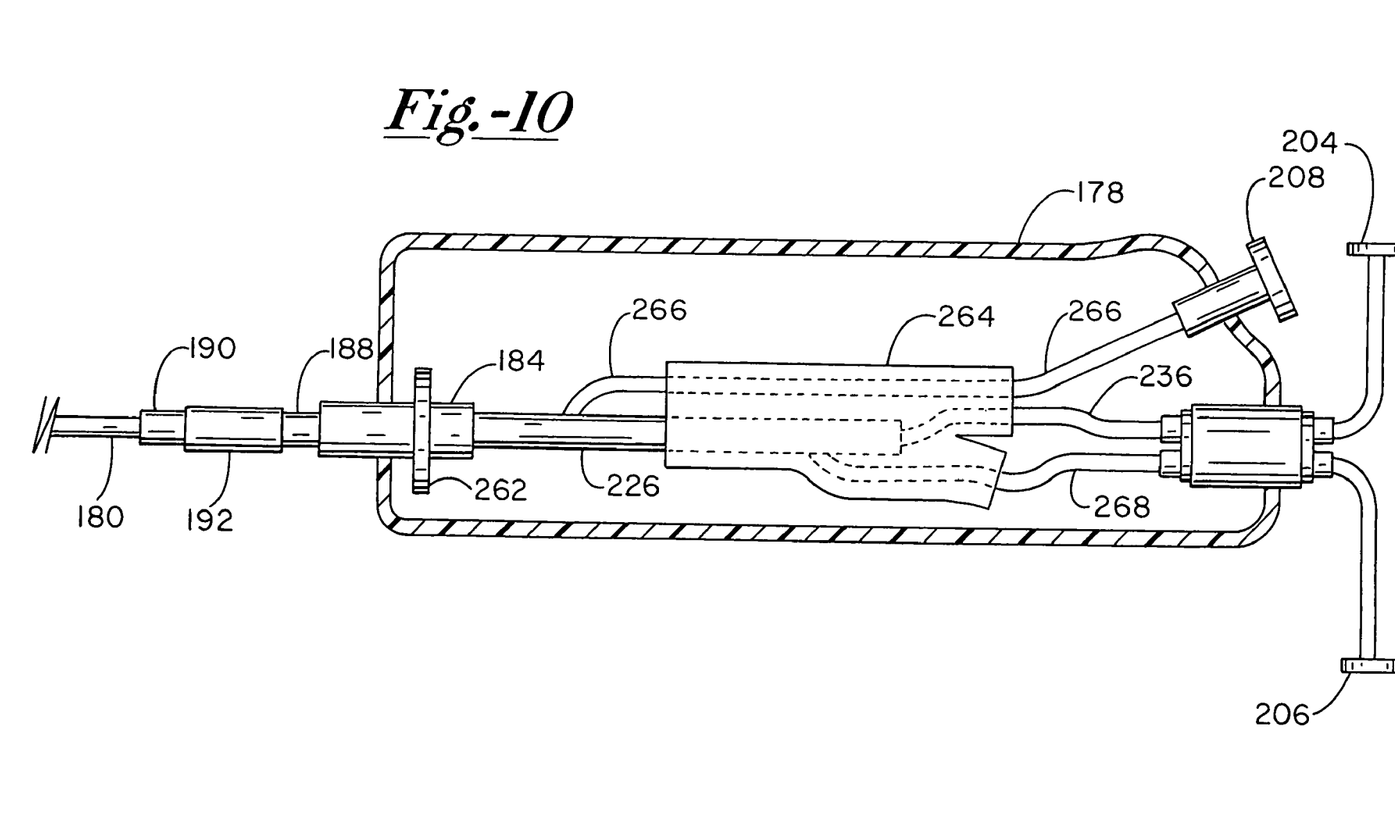
FIG. 10 is a partially sectioned view of a proximal region of the system shown in FIG. 6.

FIG. 10 shows the interior of proximal handle 178. A retaining feature 262, integral with strain relief member 184 near its proximal end, couples catheter shaft 180 to the handle and facilitates transmission of torque from the handle to the shaft. Dual lumen tube 226 extends proximally from the strain relief member to a Y adaptor 264. Distally of the Y adaptor, a proximal contrast media tube 266 is joined to tube 226, in fluid communication with D-shaped lumen 248. Tube 266 extends proximally through the Y adaptor, to proximal fluid port 208. Thus, the fluid pathway for conducting contrast media from the proximal end of system 176 to a surface of tissue within which helix 202 is embedded, includes proximal port 208, tube 266, D-shaped lumen 248 of dual lumen tube 226, and fluid passage 250.

Single lumen tube 236 extends proximally out of dual lumen tube 226 and beyond the Y adaptor 264, to proximal fluid port 204. Tube 236 is bonded to the Y adaptor at its exit point, to prevent leakage. Thus, one fluid pathway for providing fluid agents to tissue into which helix 202 is embedded includes fluid port 204, single lumen tube 236, and inner tube 230.

A proximal fluid agent tube 268 with a distal end open to D-shaped lumen 240 is bonded to Y adaptor 264, and extends proximally from the Y adaptor to proximal fluid port 206. Thus, another fluid pathway for providing fluid agents to tissue in which helix 202 is embedded includes port 206, tube 268, D-shaped lumen 240, and annular lumen 234 in the helix.

Proximal tube 266 is formed of Pebax (brand name) 7333 polyether block amide or other suitable thermoplastic elastomer. Proximal tube 268 is formed of Grilamid (brand name) transparent thermoplastic polyamide. Tubing seals are formed with UV curable 3301 epoxy. The opposite halves of handle 178 are coupled with Loctite 4013 adhesive.

In an alternative, MRI compatible version of system 176, the catheter shaft is adapted for passage through an MRI compatible deflectable guide catheter such as is disclosed in copending application Ser. No. 11/016,448 and pending application 2004/0220470. In the MRI compatible system, the ferromagnetic components are replaced with non ferromagnetic components to reduce catheter motion effects during imaging, to prevent tissue heating during imaging, and to reduce image distortion. The ferromagnetic components are replaced with materials having similar structural properties. For example, the stainless steel braid in catheter shaft medial tubing 194 may be replaced with a Nitinol or titanium braid. The substitute for coil 196 is formed of Nitinol, Titanium or MP35N, a nickel-cobalt-chromium-molybdenum alloy available from Carpenter Technology Corporation of Reading, Pa. The MP35N alloy has a tensile strength of up to 300 ksi (2068 MPa), good ductility and toughness, and resists corrosion, sulfidation, high temperature oxidation, and hydrogen embrittlement. Alternative materials include Elgiloy, Phynox and tantalum. The alternative to helix 202 is formed of Nitinol, Elgiloy or titanium.

Catheters that can be actively tracked in an MRI environment are described in U.S. Pat. No. 5,928,145. In the preferred embodiment, the coil equivalent to coil 196 of the catheter shaft becomes the active loop antenna for active MRI imaging, used in conjunction with a passive Morph (brand name) MRI compatible deflectable guiding catheter.

Certain preferred embodiment systems are capable of both fluoroscopic and MRI imaging. The helical penetrating element in these systems is made of Nitinol, and coated with gold for superior radiopacity. The C-ring element of the guide catheter, and the proximal and distal bushings may also be coated with gold for superior radiopacity. No ferromagnetic materials are used.

The catheter-based systems disclosed enable and facilitate implementation of the geometric and temporal delivery protocols described in Table 1, to deliver the therapeutic agents described in Table 2, using the controlled release strategies described in Table 3.

TABLE 1

Geometric and Temporal Delivery Protocols

| Clinical Indication | Method of Therapeutic Delivery |
| --- | --- |
| Coronary Artery Disease | Multi Focal in which a set protocol is followed to deliver apical and endocardial to the primary arterial vessels of the heart such that agents delivered will migrate up the vessels and provide for delivery in a periadventicial fashion. If a single vessel is targeted, delivery strategy would be the same as for restenosis or vulnerable plaque. Conversely a multifocal strategy could be followed for treating all vessels for vulnerable plaque and restenosis even if no specific vessel risk is identified. |
| Vulnerable Plaque | FOCAL in which the target artery region to be treated is identified by first placing a guidewire, stent or other device in the vessel and the catheter is targeted to delivery into the myocardium slightly more apical and distal to the target site in order that the endogenous drainage and transport pathways will carry agents to treat the target site. In the preferred embodiment, three or four separate distributions in the region are targeted to avoid loss of therapeutic potential due to inadvertent venous drainage. |
| Restenosis/Stenosis | FOCAL in which the target artery region to be treated is identified by first placing a guidewire, stent or other device in the vessel and the catheter is targeted to delivery into the myocardium more apical and distal to the target site in order that the endogenous drainage and transport pathways will carry agents to treat the target site. In the preferred embodiment, three or four separate distributions in the region are targeted to avoid loss of therapeutic potential due to inadvertent venous drainage. |
| Heart Failure | GLOBAL in which a set protocol is followed that includes incrementally deflecting the Morph guiding delivery catheter through its sweep and delivering at each target site by advancing the helical infusion catheter system, followed by rotating the Morph guiding delivery catheter through up to 360 degrees of its rotation and delivering at each target site by advancing the helical infusion catheter system. As shown in FIG. 3, deliveries may be performed by altering one variable at a time such that location (L) is a function of the variables rotation (R) and deflection (D). L = f(R,D) and only one variable is altered at a time such that the entire region to be treated may be targeted in a controlled repeatable fashion. |
| Ischemia | FOCAL in which the therapeutic is not delivered globally, but rather in a very local region of the myocardium near the apex of the wall region to be treated with three to four separate deliveries closely grouped to avoid loss of therapeutic potential due to inadvertent venous drainage of the target site. Goal is to maintain a region of high concentration that is distal (more apical) or within the ischemic zone to enable the concentration gradients to provide a means for chemotaxus of vessel formation. |
| AV Nodal Arrhythmias | FOCAL in which specific site is targeted. May target specific region of the AV Node such as Left Bundle or Right Bundle branch, and these most likely to be found endocardially with a bipolar electrode that exists either on the distal end of the steerable guiding catheter (preferred) or on the helical infusion catheter. |
| Hypertrophic Cardiomyopathy amenable | Diffuse but not Global delivery from within the right ventricle into the septal wall has potential to treat the tissue. Any loss of ablative media will enter the lungs and not cause potentially dangerous vascular sclerosing events on the arterial side. Preferred embodiment is to target a broader region of the septum from within the right ventricle than a typical focal delivery |

TABLE 1-continued

Geometric and Temporal Delivery Protocols

| Clinical Indication | Method of Therapeutic Delivery |
|---|---|
| to septal ablation | strategy. |
| Ischmia induced Mitral Regurgitation | FOCAL delivery of angiogenic preparations for ischemia (see Table 2) into the papillary muscle. |
| Pulmonary Vein Isolation | Focal into regions around the pulmonary veins. |

TABLE 2

Biopharmaceutical Agents for Intramyocardial Delivery

| Clinical Indication | Therapeutics | | | |
|---|---|---|---|---|
| | 1st | 2nd | 3rd | 4th |
| Heart Failure | Particulate or gel based controlled release of BNP (B-type natriuretic peptide) | Apelin protein in a controlled release particulate or gel formulation. | Stem cells that may differentiate into cardiac myocytes (Osiris, Viacell, Geron); | Autologous cardiac myocytes transplanted from RV to LV (BioCardia) |
| Restenosis and Stenosis | Particulate or gel based controlled release Arginine polymers (7 units or longer) | Particulate or gel based controlled release of Immunosuppressive agents such as Sirolimus. | Particulate or gel based controlled release of cytotoxic agents such as Taxus. | Poly-L-Argine having a length of greater than 7 arginine units in solution of PBS. |
| Ischemia | Particulate or gel based controlled release FGF-2 (or other angiogenic cytokines well known in the literature such as VEGF-121, VEGF-165, VEGF-189, HGF, PDGF, DEL-1, etc) | Adult autologous tissues derived from bone marrow or blood including: fractionated bone marrow, mesenchymal stem cells, isolated platelets, and activated platelets | Gene therapies (adenoviral, adenoassociated viral, plasmid, formulated plasmid, or liposomal mediated delivery) that provide for expression and exportation of angiogenic proteins outside cell cytosol | |
| AV Nodal Arrhythmias | Alcohol | Phenol | Gene therapies to restore cardiac ion channels or restore beta adrenergic signaling. | Angiogenic therapies targeted to ischemia (see row above) to promote tissue nutrients and waste support and eliminate ectopic foci |
| Pulmonary Vein, Superior Vena Cava, and Inferior Vena Cava initiated Supraventricular Arrhythmias | Gene therapies to restore cardiac ion channels or restore beta adrenergic signaling. | Alcohol | Phenol | Angiogenic therapies targeted to ischemia (see row above) to promote tissue nutrients and waste support and eliminate ectopic foci. |
| Hypertrophic cardiomyopathy amenable to septal ablation | Alcohol | Phenol | Anti-inflammatory agents | Natrecor/BNP, Apelin |
| Vulnerable Plaque | Collagen | Fibrin glues | Antiangiogenic agents | Statins |
| Acute Myocardial Infarction | Collagen | Elastin | Polymethylmethacrelate | Tissue adhesives |

TABLE 3

Sustained Release Strategies

| | |
|---|---|
| Particulate | Controlled release microspheres in a size range of 15 um to 200 um that can be passed down a fluidic pathway (Alkermes). |
| Gel based | Two-fluid components that set when the fluids interact, e.g. Fibrin Glue (Omrix, Baxter). |
| Gel Based | Reverse phase materials, i.e. fluids that solidify at body temperature. |
| Gel Based | Fluids that set by chemical reactions in vivo, e.g. SABER Technology (Durect Corp). |
| Solid Implant | Solid nonerodable polymer helical implant which may be delivered using a catheter nested helix design as disclosed in U.S. Pat. No. 6,478,776. |

Example 1

Treatment of Ischemia in Coronary Artery Disease

There are two preferred embodiments of this therapy. The first is to provide an angiogenic cytokine in a controlled release matrix that can be delivered with a transendocardial catheter system. As controlled release matrices such as those described in Table 3 have potential for life threatening embolic events—particularly for catheters placed within the left ventricle of the heart—the need for a stable helical needle system becomes apparent. Preferred controlled release strategies include the delivery of microspheres sized between 15 and 200 um, the delivery of fluidic gels that set up within the ventricle by either a chemical interaction or temperature change, or the delivery of helical controlled release depots that remain within the heart as described in U.S. Pat. No. 6,478,776, which patent is incorporated herein by reference.

For the first two controlled release strategies, one or more angiogenic cytokines would be placed in the controlled release matrix in either solid or fluid mixture form, and delivered in 0.2 cc aliquots at three to five sites in the apex and endocardial region of the heart, at three separate sites that are close together. Solid particulates could be delivered in a fluid suspension. Particulates also could be delivered in a viscous fluid to improve retention over time. The small volume of delivery is desirable to prevent migration within the tissue. Solid implants, either polymer or metal as described in U.S. Pat. No. 6,478,776, would also be placed at three separate sites close to one another, although other approaches could be employed.

In certain procedures, more than one region of the heart is to be treated (i.e. tissues which subtend major vessels such as the main left coronary artery or its branches the left circumflex coronary artery and the left anterior descing coronary artery, the right coronary artery and its branches the right ventricle branch of the right coronary and the acute marginal branch, anterior descending, right posterior and circumflex coronary arteries). In these procedures multiple depots (groups of fluidic or solid implants) should be positioned closer to the apex of the heart than to the base of the heart—such that the poorly perfused territories are on the basal side of the depots. For example, the procedure can involve three depots, each with three deliveries, for three distal wall regions.

An identical dosing strategy could be provided for either angiogenic autologous tissues such as autologous bone marrow, described in pending U.S. patent applications, publication numbers 2002/0037278 and 2004/0161421, and in the relevant literature. Unique in this approach is the delivery of angiogenic autologous tissue intramyocardially at three to five sites, with sites targeted towards the apical third of the left ventricle.

Example 2

Heart Failure—Global Delivery

Heart failure treatment is fundamentally different from therapy for ischemia, and requires broader treatment. The preferred embodiments involve the broad delivery of controlled release formulations of proteins known to be involved in heart failure signaling. Two such agents are BNP (B-type natriuretic peptide) which is released endogenously from the myocytes in heart failure, and apelin which reduces blood pressure via a nitric oxide dependent mechanism. Apelin also is a potent stimulator of cardiac contractility. In the delivery strategy, controlled release BNP (nesiritide), available from Scios Inc. of Freemont, Calif. under the brand name Natrecor, apelin, or both can be delivered to sites within the heart broadly following a grid pattern such that the catheter is positioned and moved through a preset series of steps to target an entire region. For example, if the initial site is in the apex and the catheter is to deliver to all regions within the left ventricle, the device is used to deliver the fluid agent over a first area, the guide is deflected, and delivery occurs to a second area. The guide is then deflected further and a third delivery occurs, then rotated slightly for a fourth delivery. Straightening the guide in two steps allows delivery of the fifth and sixth aliquots. By using a system with three degrees of freedom, set protocols of deflection and rotation may be used to effect deliveries in a repeatable and efficient fashion globally to broad regions of the ventricles. In many cases, only one ventricular wall such as the lateral free wall or the posterior wall will be targeted, but the process can be identical.

Example 3

Focal Deliveries

Focal deliveries for restenosis/stenosis, nodal Arrhythmias, ischemia induced mitral regurgitation, vulnerable plaque and the like, require one to three deliveries close to one another of the preferred therapeutic strategy at the target area. For restenosis/stenosis, vulnerable plaque, and the like, the target is a large epicardial vessel. To deliver to this vessel target, delivery should be performed distal (apical) to the target and in line with the target such that the putative therapeutics from table 2 as well as others not specified here may migrate towards the epicardium and up to the vessel wall periadventicially. It is not well recognized that the lymphatic vessels in the human heart migrate along and around the coronary arteries and that periadventicial delivery may be enabled to a target zone through intramyoicardial delivery distal to the target zone.

Example 4

Diffuse Delivery

Diffuse but not focal strategies are appropriate where one target wall region is intended to be treated, such as in hypertrophic cardiomyopathy. Delivery from the right ventricle is safe and many locations within the wall zone can be targeted (potentially on repeat occasions) with agents designed to reduce the wall thickness. Although ablative agents such as alcohol and phenol are preferred because of their current use via a transarterial route, the delivery of agents that reduce tissue inflammation, and agents that may prevent heart failure such as Apelin and BNP may also be employed.

The clinical indications in table 1 may be treated with any of the putative therapeutic agents as described in table 2 using controlled release strategies in table 3. Transendocardial catheter systems such as those described herein enable many of these therapeutic strategies for the first time.

What is claimed is:

1. A process for locally treating tissue at a treatment site inside the body, including:
   using an elongate catheter having a fluid delivery structure at its distal end to guide the fluid delivery structure to an intended treatment site inside the body, and causing a penetrating element of the fluid delivery structure to penetrate tissue to a first depth at the treatment site; and
   with the penetrating element penetrated to the first depth, supplying a first fluid agent comprising a therapeutic agent to surrounding tissue via a first fluid passage through the fluid delivery structure open to an exterior thereof along the tissue penetrating element, to deliver the first fluid agent for infusion into the surrounding tissue at a selected depth within the tissue; further with the penetrating element penetrated to the first depth, supplying a second fluid agent to the tissue via a second fluid passage through the fluid delivery structure open to said exterior along the tissue penetrating element, to deliver the second fluid agent for infusion into the surrounding tissue at the selected depth to commingle the first and second fluid agents within the tissue, to provide a matrix within the tissue for effecting a controlled release of the therapeutic agent.

2. The process of claim 1 including:
causing the penetrating element to penetrate surrounding tissue at a plurality of different locations in the tissue, and supplying the first fluid agent and the second fluid agent substantially at the selected depth within the surrounding tissue at all of the different locations, to effect a global delivery of the fluid agents.

3. The process of claim 1 wherein:
supplying the first fluid agent comprises supplying a suspension of microspheres in the first fluid agent to provide a controlled release matrix.

4. The process of claim 1 wherein:
delivering the fluid agents comprises performing a step from the group consisting of: (i) selecting the first and second fluid agents whereby the first and second agents are adapted to form a gel upon interacting with one another; (ii) selecting, as the first fluid agent, a fluid agent that is chemically reactive in vivo to form a gel; and (iii) selecting, as the first fluid agent, a fluid agent that is adapted to solidify at body temperature.

5. The process of claim 1 wherein:
delivering the first and second fluid agents comprises selecting first and second fluid agents whose viscosity tends to increase upon delivery to the surrounding tissue.

6. The process of claim 1 wherein:
the therapeutic agent is selected from the group consisting of: cell, protein, and gene based therapeutics.

7. The process of claim 1 wherein:
causing the penetrating element to penetrate tissue comprises using a penetrating element shaped as a helix.

8. A process for locally treating tissue at a treatment site and visualizing the treatment site, including:
using an elongate catheter having an electrically conductive fluid delivery component at its distal end and an electrically conductive electrode proximate the distal end and electrically isolated from the fluid delivery component, to guide the fluid delivery component to an intended treatment site inside the body and causing a penetrating element of the fluid delivery component to penetrate surrounding tissue at the treatment site;
with the penetrating element so penetrated, supplying a contrast fluid to a first location in the tissue, via a first fluid passage through the fluid delivery component;
further with the penetrating element so penetrated, using the fluid delivery component and the conductive electrode to effect a bipolar sensing of electrical activity in tissue at the intended treatment site; and
further with the penetrating element so penetrated, supplying a first fluid agent to a second location in the tissue at a depth within the surrounding tissue near the penetrating element, via a second fluid passage through the fluid delivery component.

9. The process of claim 8 wherein:
supplying the first fluid agent comprises supplying a suspension of microspheres in the first fluid agent to provide a controlled release matrix.

10. The process of claim 8 wherein:
supplying the first fluid agent comprises performing a step from the group consisting of: (i) selecting, as the first fluid agent, a fluid agent that is chemically reactive in vivo to form a gel; and (ii) selecting, as the first fluid agent, a fluid agent that is adapted to solidify at body temperature.

11. The process of claim 8 wherein:
the therapeutic agent is selected from the group consisting of: cell, protein, and gene based therapeutics.

12. The process of claim 8 including:
further with the penetrating element so penetrated, supplying a second fluid agent to a third location in the tissue at a depth within the surrounding tissue near the penetrating element via a third fluid passage through the fluid delivery component.

13. The process of claim 12 wherein:
supplying the first and second fluid agents comprises selecting first and second fluid agents whose viscosity tends to increase upon delivery to the surrounding tissue.

14. The process of claim 12 wherein:
supplying the first and second fluid agents comprises selecting first and second fluid agents having respective first and second viscosities that differ by at most twenty-five percent.

15. The process of claim 12 wherein:
supplying the first and second fluid agents comprises selecting first and second fluid agents adapted to form a gel upon interacting with one another.

16. The process of claim 12 wherein:
said second and third locations substantially coincide.

17. The process of claim 8 wherein:
supplying the contrast fluid to the first location comprises supplying the contrast fluid to a surface of the tissue at the treatment site.

18. A process for contemporaneously delivering a plurality of fluid agents at a depth within tissue at a selected site inside the body, including:
guiding a fluid supply structure to an intended treatment site inside the body, and causing a tissue penetrating element of the structure to penetrate tissue to a first depth at the treatment site;
with the penetrating element penetrated to the first depth, supplying a first fluid agent to the tissue via a first fluid passage through the fluid supply structure open to an exterior of the fluid supply structure at a first location along the penetrating element, thus to infuse the first fluid agent into selected tissue adjacent and about the penetrating element; and
further with the penetrating element so penetrated, supplying a second fluid agent via a second fluid passage extending through the fluid supply structure, coaxial with the first fluid passage and open to said exterior at a second location along the penetrating element, thus to infuse the second fluid agent into the selected tissue adjacent and about the penetrating element while preventing any substantial intermingling of the first and second fluid agents upstream of the first and second locations when the first and second fluid agents are contemporaneously supplied;
wherein supplying the first fluid agent comprises supplying a suspension of microspheres in the first fluid agent to provide a controlled release matrix.

19. The process of claim 18 wherein:
delivering the fluid agents comprises performing a step from the group consisting of: (i) selecting the first and second fluid agents whereby the first and second agents are adapted to form a gel upon interacting with one another; (ii) selecting, as the first fluid agent, a fluid agent that is chemically reactive in vivo to form a gel; and (iii) selecting, as the first fluid agent, a fluid agent that is adapted to solidify at body temperature.

20. The process of claim 18 wherein:
the therapeutic agent is selected from the group consisting of: cell, protein, and gene based therapeutics.

21. The process of claim 18 wherein:
delivering the first and second fluid agents comprises selecting first and second fluid agents whose viscosity tends to increase upon delivery to the surrounding tissue.

22. The process of claim 18 wherein:
causing the penetrating element to penetrate tissue comprises using a penetrating element shaped as a helix.

23. The process of claim 22 wherein:
guiding the fluid supply structure comprises using an elongate catheter having the fluid supply structure disposed at its distal end to guide the fluid supply structure to the intended treatment site.

24. The process of claim 18 wherein:
the second fluid passage is surrounded by the first fluid passage, and the second location is disposed at a distal end of the second fluid passage recessed proximally relative to the first location to facilitate an intermingling of the first and second fluid agents in the first fluid passage between the first and second locations when the first and second fluid agents are contemporaneously supplied.

25. The process of claim 18 wherein:
the first and second locations substantially coincide at a distal tip of the penetrating element.

26. A process for simultaneously delivering a plurality of fluid agents at a depth within tissue at a selected site inside the body, including:
guiding a fluid supply structure to an intended treatment site inside the body, and causing a tissue penetrating element of the structure to penetrate tissue to a first depth at the treatment site;
with the penetrating element penetrated to the first depth, supplying a first fluid agent to the tissue via a first fluid passage through the fluid supply structure open to an exterior of the fluid supply structure at a first location along the penetrating element, thus to infuse the first fluid agent into selected tissue adjacent and about the penetrating element; and
further with the penetrating element so penetrated, supplying a second fluid agent via a second fluid passage extending through the fluid supply structure, coaxial with the first fluid passage, surrounded by the first fluid passage, and open to said exterior at a second location along the penetrating element either coincident with or recessed proximally relative to the first location, thus to infuse the second fluid agent into the selected tissue adjacent and about the penetrating element while preventing any substantial intermingling of the first and second fluid agents upstream of the first and second locations when the first and second fluid agents are contemporaneously supplied.

27. The process of claim 26 wherein:
supplying the first fluid agent comprises supplying a suspension of microspheres in the first fluid agent to provide a controlled release matrix.

28. The process of claim 26 wherein:
delivering the fluid agents comprises performing a step from the group consisting of: (i) selecting the first and second fluid agents whereby the first and second agents are adapted to form a gel upon interacting with one another; (ii) selecting, as the first fluid agent, a fluid agent that is chemically reactive in vivo to form a gel; and (iii) selecting, as the first fluid agent, a fluid agent that is adapted to solidify at body temperature.

29. The process of claim 26 wherein:
the therapeutic agent is selected from the group consisting of: cell, protein, and gene based therapeutics.

30. The process of claim 26 wherein:
delivering the first and second fluid agents comprises selecting first and second fluid agents whose viscosity tends to increase upon delivery to the surrounding tissue.

31. The process of claim 26 wherein:
causing the penetrating element to penetrate tissue comprises using a penetrating element shaped as a helix.

32. The process of claim 31 wherein:
guiding the fluid supply structure comprises using an elongate catheter having the fluid supply structure disposed at its distal end to guide the fluid supply structure to the intended treatment site.

* * * * *